United States Patent
Ran

(10) Patent No.: US 10,041,906 B2
(45) Date of Patent: Aug. 7, 2018

(54) ELECTROPHORESIS AND ELECTROBLOTTING SYSTEMS AND METHODS

(71) Applicant: Bio-Rad Laboratories, Inc., Hercules, CA (US)

(72) Inventor: Boaz Ran, Haifa (IL)

(73) Assignee: Bio-Rad Laboratories, Inc., Hercules, CA (US)

( * ) Notice: Subject to any disclaimer, the term of this patent is extended or adjusted under 35 U.S.C. 154(b) by 224 days.

(21) Appl. No.: 15/059,093

(22) Filed: Mar. 2, 2016

(65) Prior Publication Data

US 2016/0258903 A1    Sep. 8, 2016

Related U.S. Application Data

(60) Provisional application No. 62/127,650, filed on Mar. 3, 2015.

(51) Int. Cl.
  *G01N 27/453* (2006.01)
  *G01N 27/447* (2006.01)

(52) U.S. Cl.
  CPC . *G01N 27/44747* (2013.01); *G01N 27/44739* (2013.01)

(58) Field of Classification Search
  CPC .................. G01N 27/44704; G01N 27/44739
  See application file for complete search history.

(56) References Cited

U.S. PATENT DOCUMENTS

| | | | |
|---|---|---|---|
| 3,803,020 A * | 4/1974 | Stephan | G01N 27/44773 422/82.01 |
| 4,385,974 A * | 5/1983 | Shevitz | G01N 27/44773 204/464 |
| 4,443,319 A | 4/1984 | Chait et al. | |
| 4,889,606 A | 12/1989 | Dyson et al. | |
| 4,994,166 A | 2/1991 | Fernwood et al. | |
| 5,234,559 A | 8/1993 | Collier et al. | |
| 5,284,559 A | 2/1994 | Lim et al. | |
| 5,449,446 A | 9/1995 | Verma et al. | |
| 6,203,679 B1 | 3/2001 | Bouis et al. | |
| 8,361,293 B2 * | 1/2013 | Wang | G01N 27/44704 204/466 |
| 9,664,646 B2 * | 5/2017 | McKee | G01N 27/44747 |
| 2007/0284250 A1 | 12/2007 | Magnant et al. | |

(Continued)

FOREIGN PATENT DOCUMENTS

| | | |
|---|---|---|
| WO | 2003/016896 A1 | 2/2003 |
| WO | 2013/180637 A1 | 5/2013 |
| WO | 2013/180638 A1 | 5/2013 |

(Continued)

OTHER PUBLICATIONS

PCT/US2016/020441, "International Search Report and Written Opinion", dated May 6, 2016, 14 pages.

*Primary Examiner* — Alexander S Noguerola
(74) *Attorney, Agent, or Firm* — Kilpatrick Townsend and Stockton LLP

(57) ABSTRACT

Integrated electrophoresis and electroblotting systems and methods are provided. In one embodiment, a cassette includes a separation gel and a sheet adjacent to a surface of the separation gel, wherein the sheet is configured to be removed from the cassette without opening the cassette. Systems and methods are also described and illustrated.

19 Claims, 14 Drawing Sheets

(56) References Cited

U.S. PATENT DOCUMENTS

2014/0027284 A1 1/2014 McKee et al.
2014/0138248 A1 5/2014 McKee et al.

FOREIGN PATENT DOCUMENTS

| WO | 2013/180639 A1 | 5/2013 |
| WO | 2013/180640 A1 | 12/2013 |
| WO | 2013/180641 A1 | 12/2013 |
| WO | 2013/180642 A1 | 12/2013 |

* cited by examiner

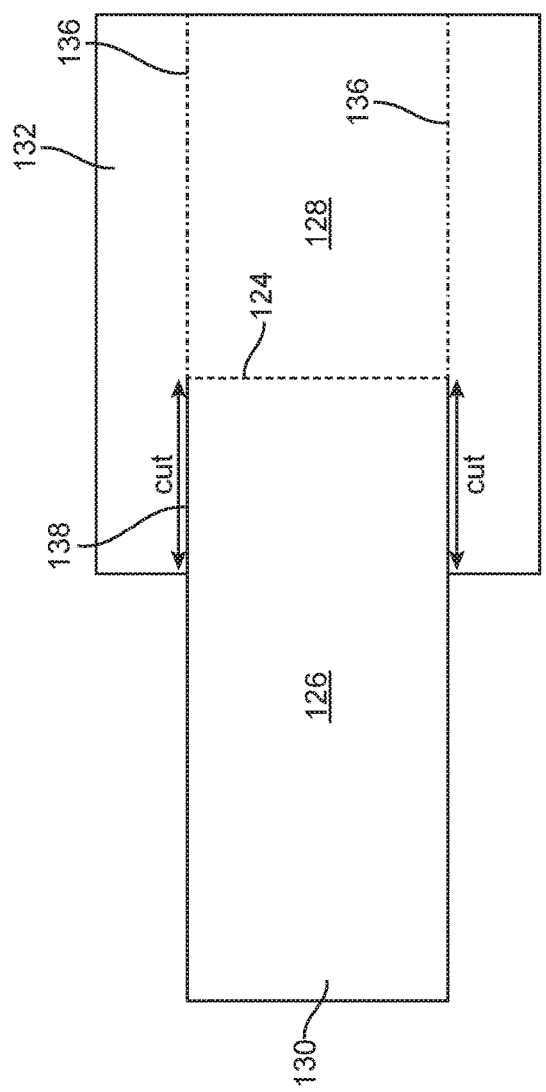
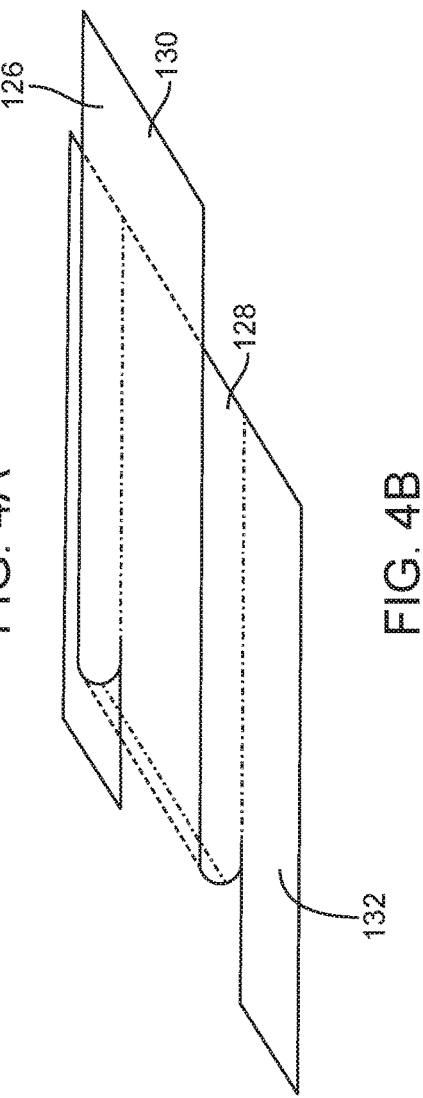
FIG. 4A
FIG. 4B

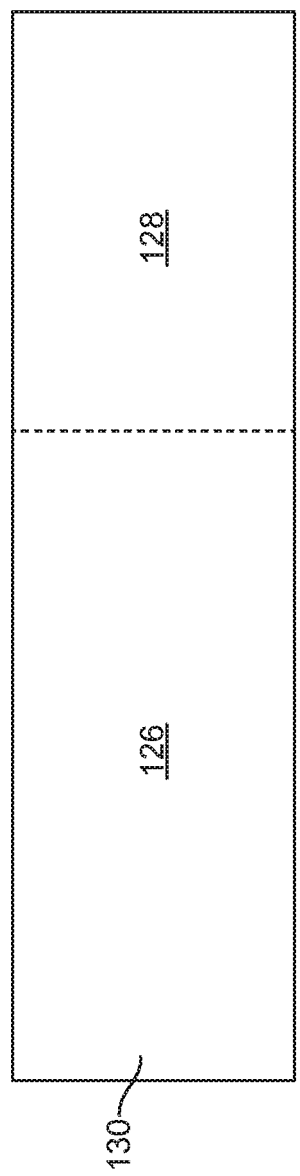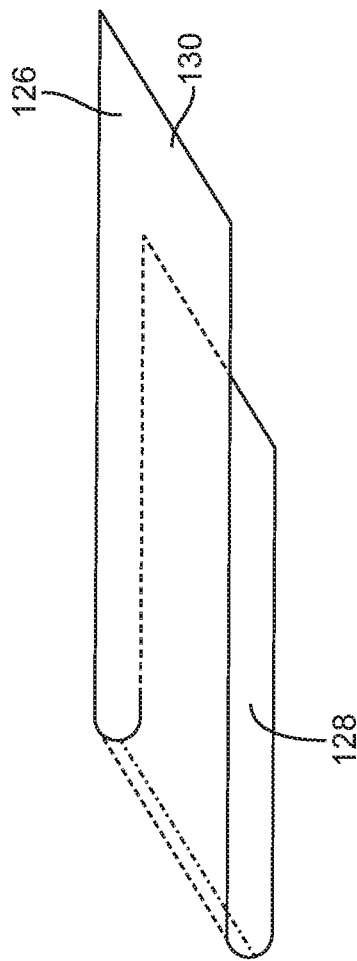
FIG. 5A
FIG. 5B

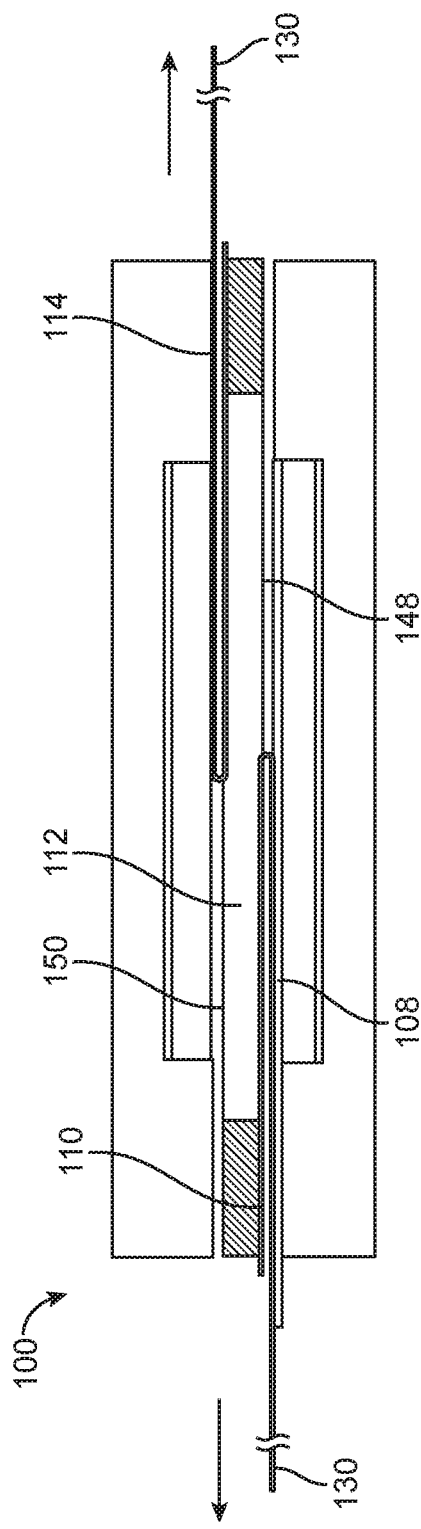
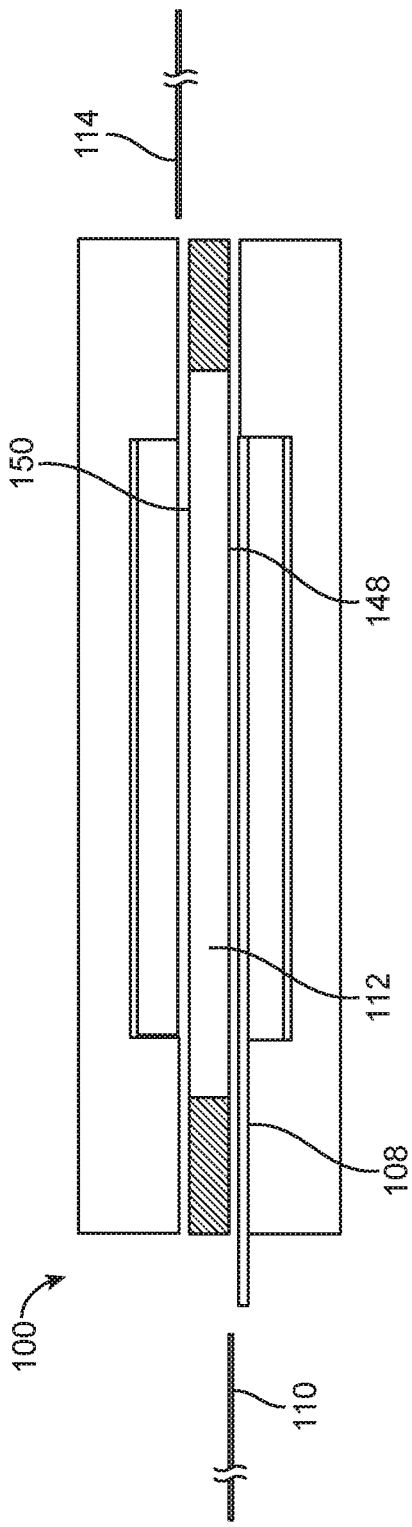

ELECTROPHORESIS AND ELECTROBLOTTING SYSTEMS AND METHODS

CROSS-REFERENCES TO RELATED APPLICATIONS

This application claims priority to U.S. Provisional Application No. 62/127,650, filed Mar. 3, 2015, which is incorporated by reference herein in its entirety for all purposes.

TECHNICAL FIELD

This invention relates to systems and methods for performing both electrophoresis and electroblotting of samples of proteins, DNA or RNA.

BACKGROUND OF THE INVENTION

Polyacrylamide gel electrophoresis (PAGE) is a useful technique for analyzing biological macromolecules such as proteins or nucleic acids. PAGE separates biological molecules based on their electrophoretic mobility, which is a function of the charge, size, and conformation of the molecule.

Blotting is a process used to transfer macromolecules from a gel to a membrane for further analysis. Molecules can be transferred from a gel to a membrane by capillary action or by electrophoretic blotting (or electroblotting).

Electrophoresis and electroblotting are usually performed in separate apparatuses because the direction of electrophoresis is in a plane that is perpendicular to the direction of electroelectroblotting. After electrophoresis, the cassette plates (i.e., glass or plastic plates) used to contain the gel act as insulators and must be removed prior to electroblotting. After the gel is removed from the cassette, the gel is placed in intimate contact with the transfer membrane without introducing air bubbles, requiring a high level of technical skill. When the gel is thin and fragile, the process of preparing the gel for electroblotting is difficult, requires a highly skilled experimenter, and introduces variability in the transfer results.

Although electrophoresis and electroblotting provide useful information, the techniques are poorly suited for integrating and automating.

BRIEF SUMMARY OF THE INVENTION

Disclosed herein are integrated electrophoresis and electroblotting systems and methods of using such systems.

In an embodiment, a combined electrophoresis and electroblotting cassette includes a separation gel and a sheet adjacent to a surface of the separation gel, wherein the sheet is configured to be removed from the cassette without opening the cassette. In embodiments, the sheet is folded along a folding line. In some embodiments, the sheet further includes a section. In some embodiments, the section is wing-shaped. In some embodiments, the section is at least partially wrapped around an outer surface of a support. In certain embodiments, the section is adhered to a surface of the support. In some embodiments, the sheet includes a pulling edge or tab. In embodiments, a gel-facing surface of the sheet is coated with a barrier coating. In some embodiments, the barrier coating is selected from the group consisting of polyvinylidene chloride, low-density polyethylene, and an acrylonitrile methyl acetate copolymer. In embodiments, the cassette further includes a membrane sandwiched between the sheet and a pad. In some embodiments, the membrane is configured to be removed from the cassette without opening the cassette. In certain embodiments, the membrane includes a pulling edge. In some embodiments, the cassette further includes a set of transfer electrodes. In some embodiments, the cassette further includes a first set of electrodes and a second set of electrodes. In certain embodiments, the cassette further includes separation electrodes and transfer electrodes.

In an embodiment, an integrated electrophoresis and electroblotting method includes removing a sheet from a cassette having a separation gel with previously separated molecules, wherein the sheet is configured to be removed from the cassette without opening the cassette; and responsive to applying an electric field normal to an electrophoretic plane of the separation gel, transferring the molecules to a membrane.

In some embodiments, an integrated electrophoresis and electroblotting system includes a cassette comprising a separation gel; a sheet adjacent to a surface of the separation gel, wherein the sheet is configured to be removed from the cassette without opening the cassette; a membrane sandwiched between the sheet and a pad; a first and second set of electrodes; and circuitry operably connected to the first and second set of electrodes and configured to apply a first electric field within an electrophoretic plane of the separation gel and a second electric field normal to the electrophoretic plane of the separation gel. In some embodiments, the system further includes at least one of a power source, a voltage source, a manual sheet extractor, a motorized sheet extractor, a pump connected to one or more reservoirs, a pump connected to waste, a manual membrane extractor, a motorized membrane extractor, a line array detector and an imager.

BRIEF DESCRIPTION OF THE DRAWINGS

FIGS. 4A and 4B show schematic top and perspective views, respectively, of a sheet according to an embodiment of the invention in which the sheet includes wings. FIG. 4A illustrates the sheet prior to folding and FIG. 4B illustrates the sheet after the sheet is folded along a folding line that is perpendicular to the longitudinal axis of the sheet.

FIGS. 5A and 5B show schematic top and perspective views, respectively, of a sheet according to an embodiment of the invention in which the sheet does not include wings. FIG. 5A illustrates the sheet prior to folding and FIG. 5B illustrates the sheet after the sheet is folded along a folding line that is perpendicular to the longitudinal axis of the sheet.

FIGS. 7A and 7B show schematic cross-sectional top views of a cassette during and after removing sheets from the cassette according to an embodiment of the invention.

The wings of the sheet are wrapped around an outer surface of a support of the cassette. The support is omitted for clarity.

Figure 10:
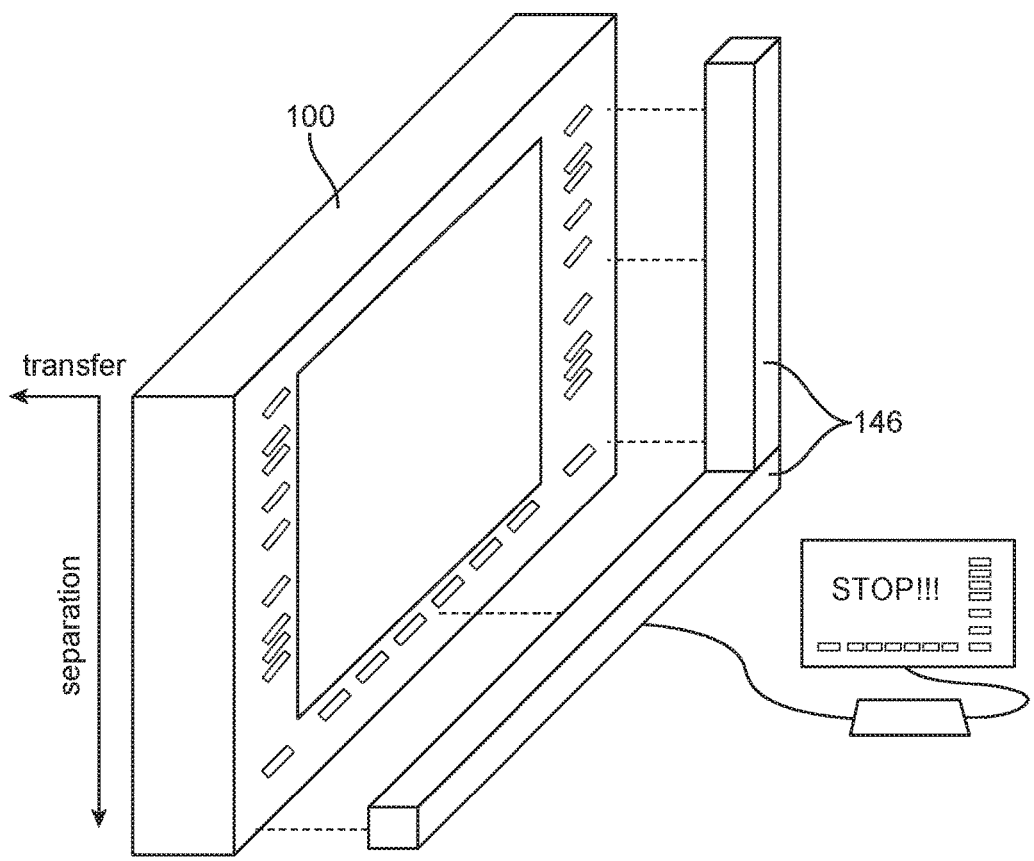

FIG. 10 shows a schematic perspective view of a system having at least one line array detector according to an embodiment of the invention.

Figure 11:
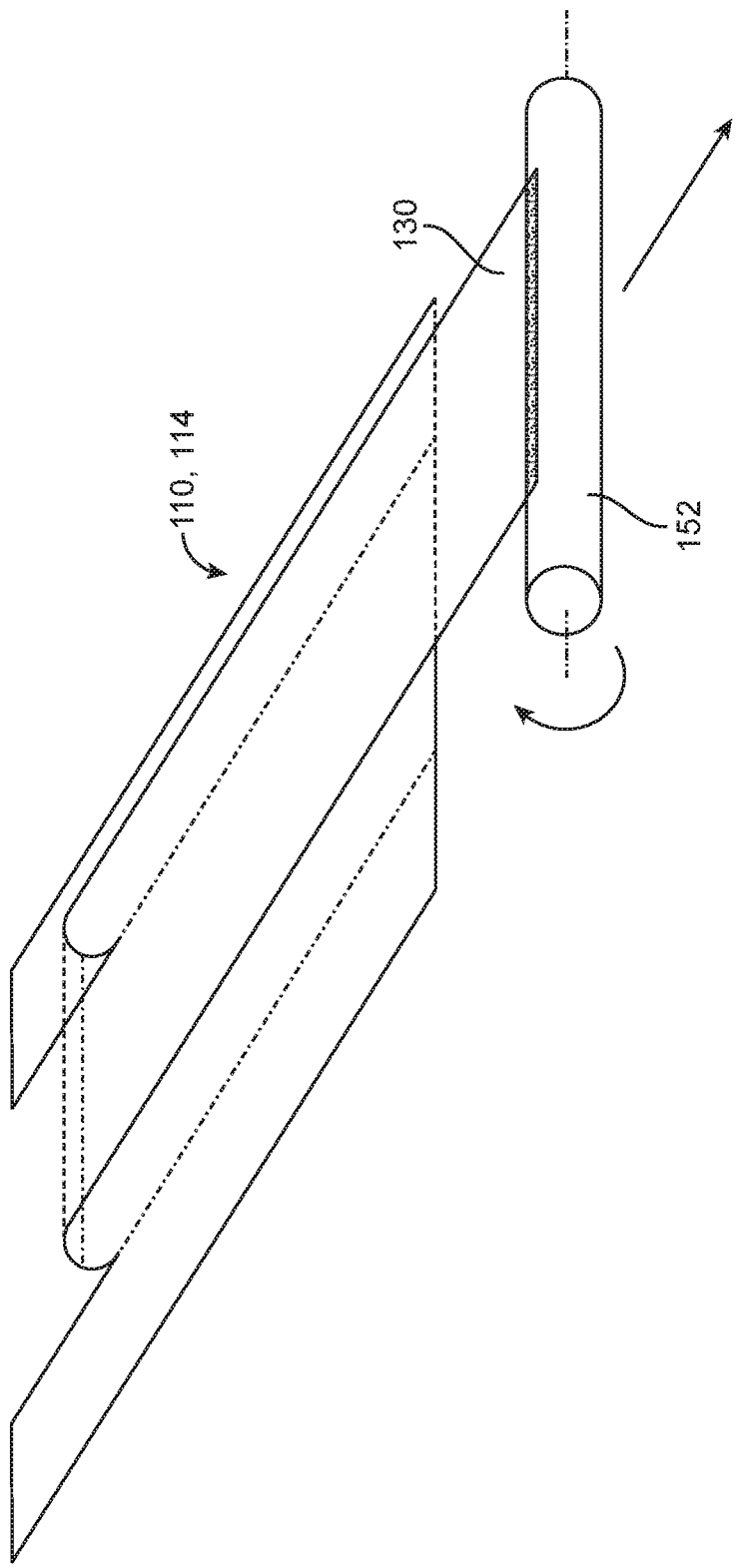

FIG. 11 shows a schematic perspective view of the sheet of FIG. 4B during a mechanical or manual removal process according to an embodiment of the invention. The sheet may be removed from the cassette with linear or rotational forces.

Figure 12:
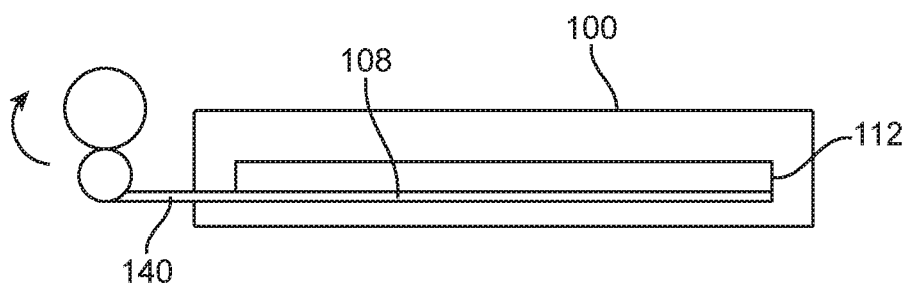

FIG. 12 is a simplified cross-sectional side view of a cassette showing a method of extracting a membrane according to an embodiment of the invention. For clarity, only the gel and membrane are shown in the cassette.

Figure 13:
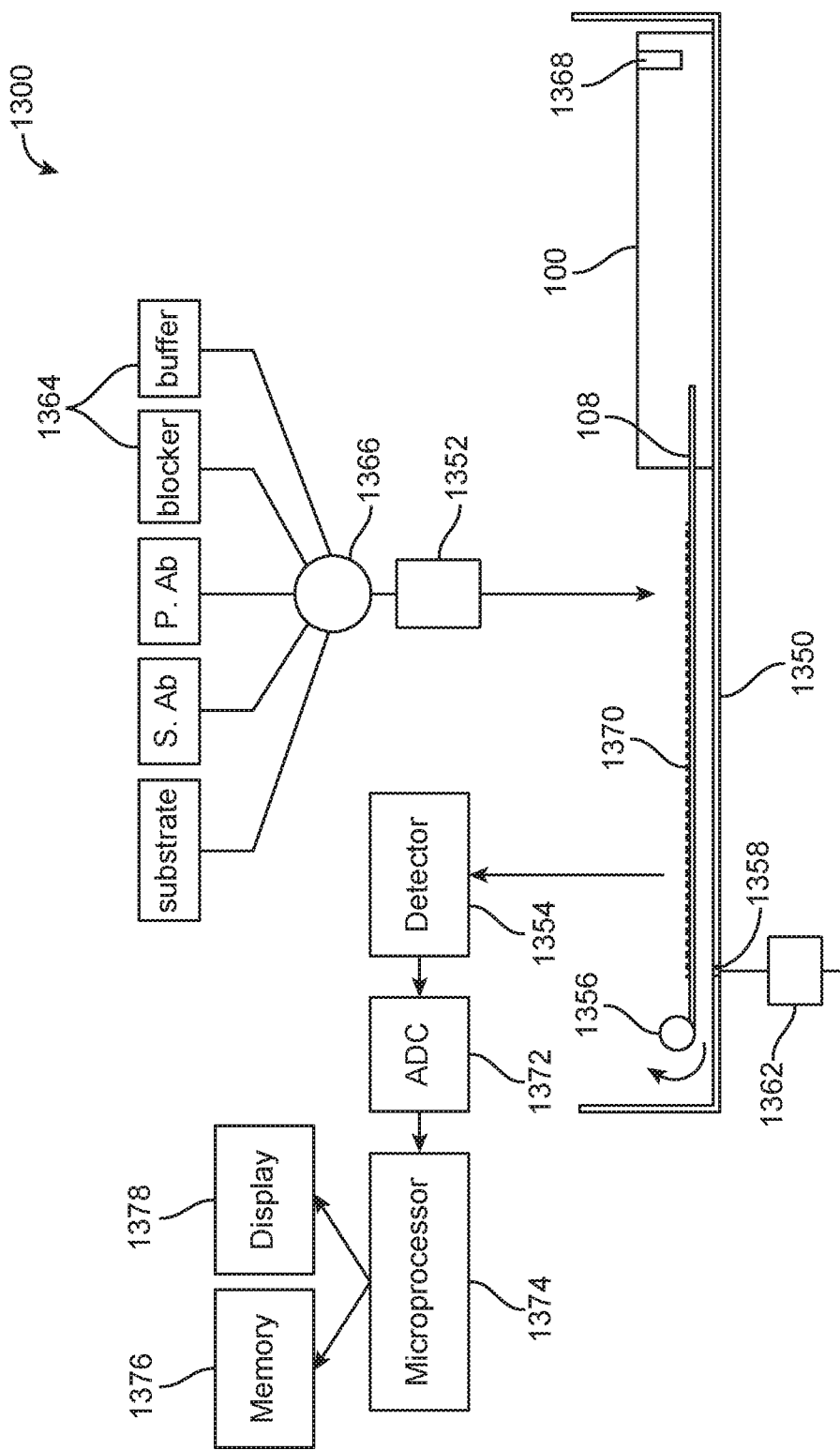

FIG. 13 shows a schematic view of an automated system according to an embodiment of the invention.

DETAILED DESCRIPTION OF THE INVENTION

Described herein are systems and methods for electrophoresis and electroblotting. The systems and methods facilitate the integration and automation of electrophoresis and electroblotting. Systems and methods have been discovered in which a sheet separating a transfer membrane from a separation gel can be removed without having to open the combined electrophoresis and electroblotting cassette.

Advantages of the system and methods described herein include, but are not limited to: (1) providing systems capable of performing both electrophoresis and blotting without having to disassemble the combined electrophoresis and blotting cassette; (2) providing systems that are "hands-free" in which no handling of the electrophoresis gel or transfer membrane is required.; (3) providing systems capable of performing blotting of proteins and nucleic acid fragments; (4) providing systems in which sheets separating the electrophoresis gel from the transfer membrane and transfer pad include a fold that facilitates removal of the sheet without tearing of the electrophoresis gel; and (5) providing systems in which the electrophoresis components (i.e., separation electrodes, separation buffer, gel) are separated electrically and mechanically from the blotting components (i.e., transfer electrodes, transfer buffer, and membrane). The electrophoresis components and blotting components are separated electrically to prevent an electrical short and are separated mechanically to prevent the different buffers from mixing.

As used in this specification and the appended claims, the singular forms "a", "an", and "the" include plural referents unless the content clearly dictates otherwise. Thus, for example, reference to a system comprising "a sheet" includes systems comprising one or more sheets solutions. Likewise, reference to "a section" includes one or more sections.

Cassette

Referring to FIGS. 1A-3, a cassette 100 for electrophoresis and electroblotting is illustrated. The cassette 100 is configured to perform gel electrophoresis in an electrophoretic plane and to perform blotting (e.g., Western, Northern or Southern blotting) in a direction perpendicular to the electrophoretic plane. The cassette 100 is generally rectangular in shape and is a "sandwich" or stack of components including a first support 102, a transfer anode 104, a first pad 106, a membrane 108, a first sheet 110, a separation gel 112, a second sheet 114, a second pad 116, a transfer cathode 118, and a second support 120.

Figure 1A:
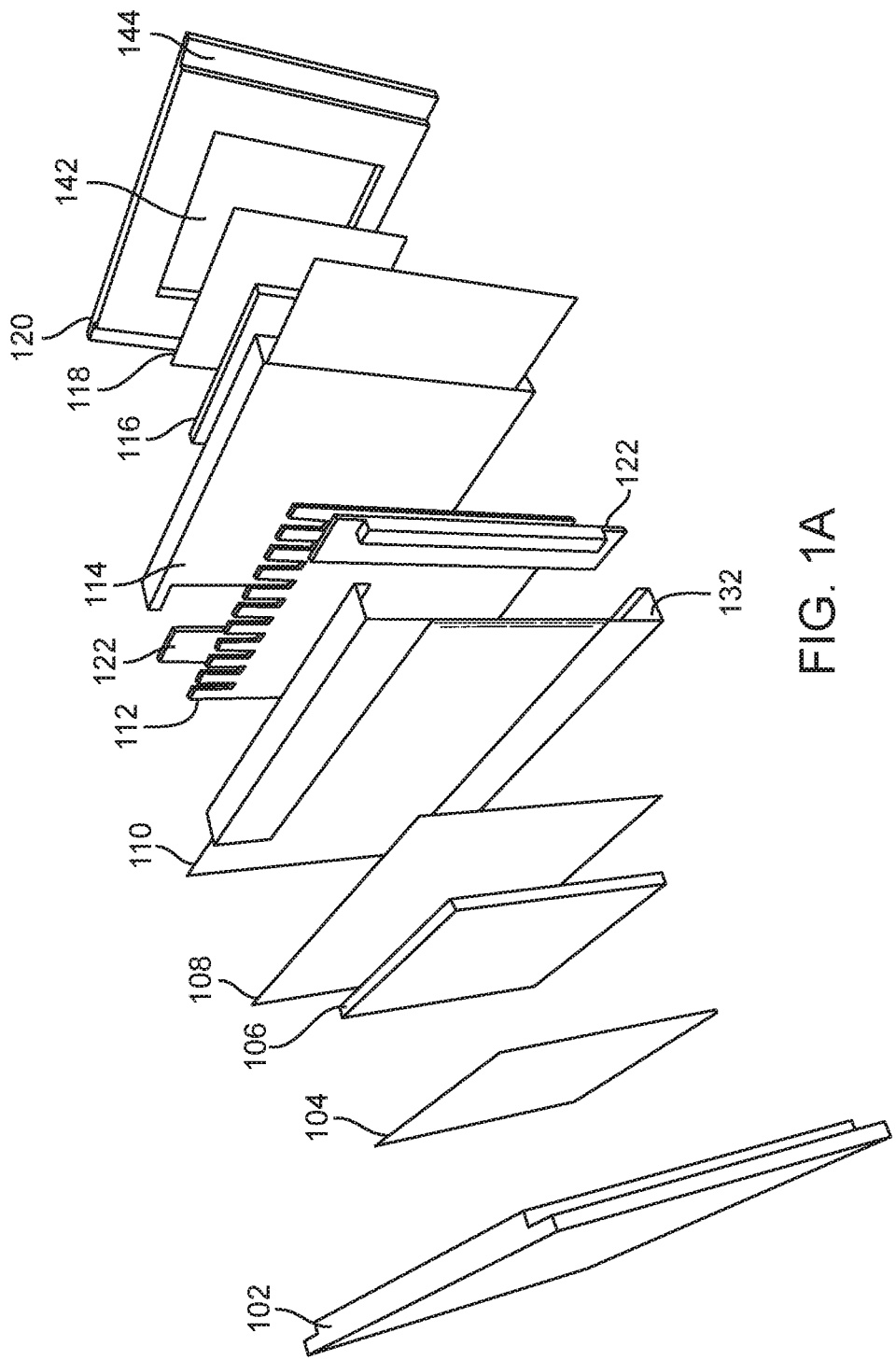
FIGS. 1A and 1B show exploded and perspective views, respectively, of a cassette according to an embodiment of the invention.
Figure 2:
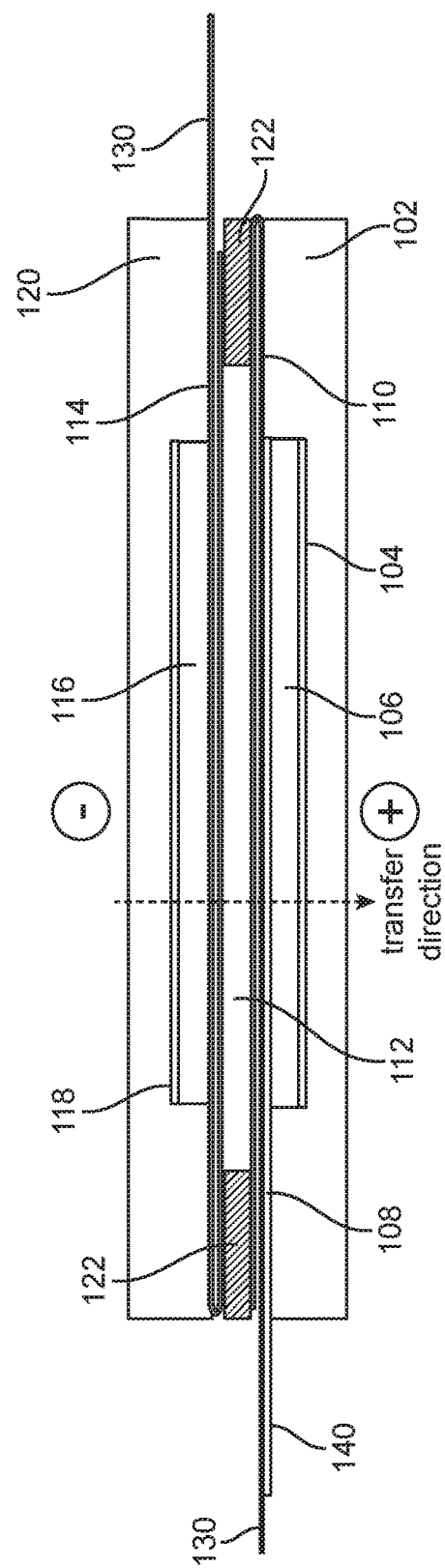
FIGS. 2 and 3 show schematic cross-sectional top and side views, respectively, of the cassette of FIGS. 1A and 1B.
Figure 3:
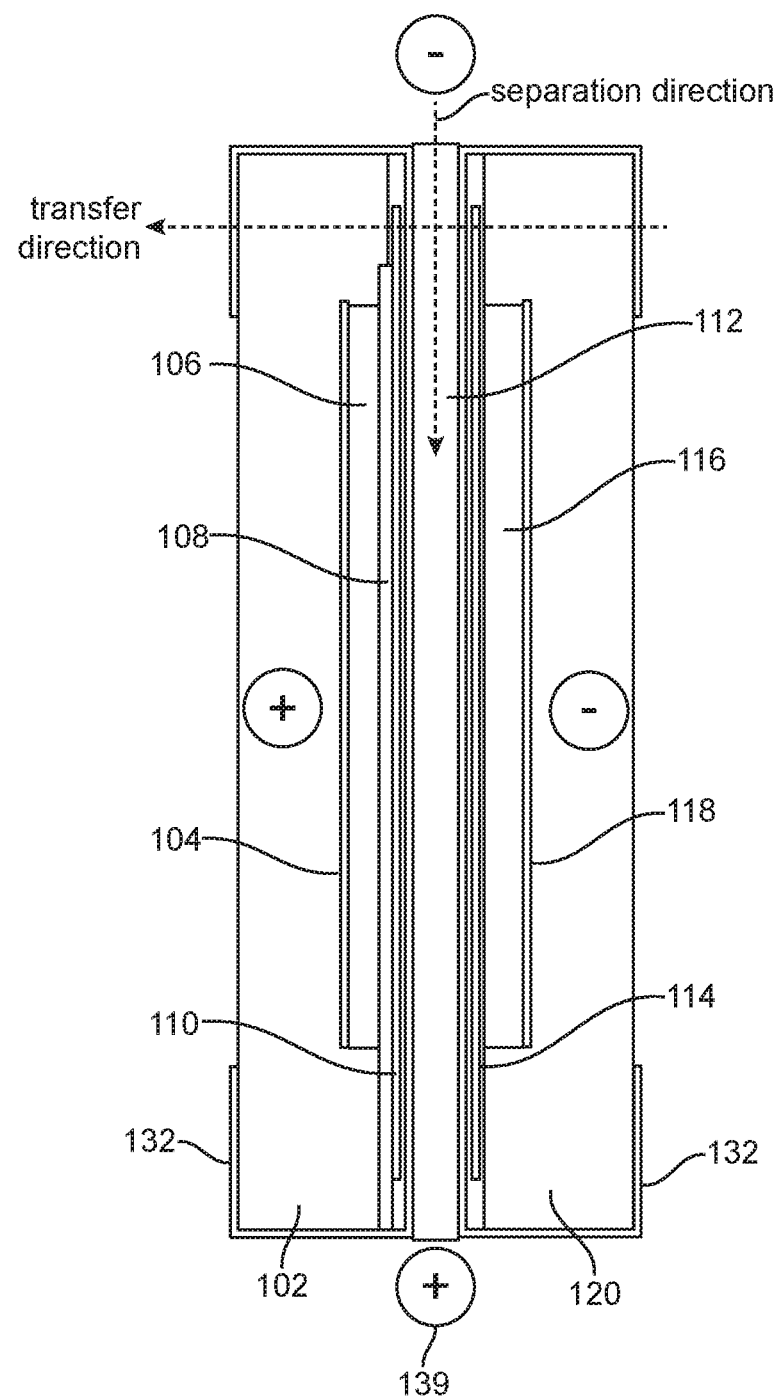
Figure 6:
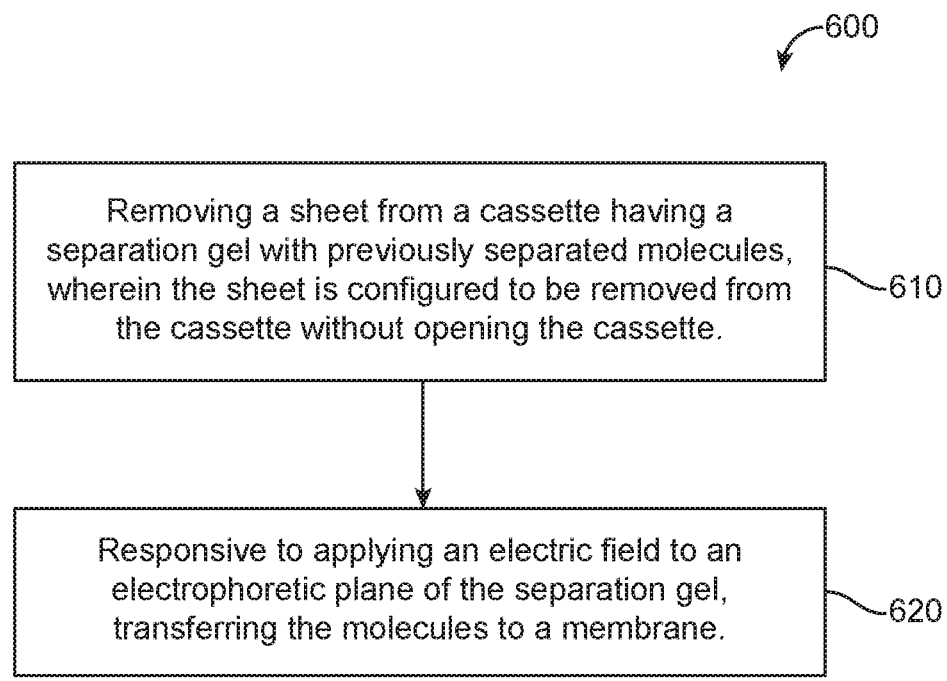
FIG. 6 is a flow chart showing a method of removing a sheet from an unopened cassette having a separation gel with previously separated molecules according to an embodiment of the invention.

As illustrated in FIGS. 1A, 2 and 3, the separation gel 112 (e.g., a polyacrylamide gel or an agarose gel) is sandwiched between the first sheet 110 and the second sheet 114. The separation gel 112 may be a pre-cast or manually prepared gel. The separation gel 112 is contained by lateral spacer strips 122.

The first and second sheets 110, 114 are configured to be removed from the cassette 100 without opening the cassette 100. In embodiments (see FIGS. 4A-5B), each of the sheets is folded along a folding line 124 located perpendicular to a longitudinal axis of the sheet. The fold in each sheet facilitates pealing (rather than pulling) of the sheet from the surface of the gel, which can prevent tears in the gel. The folding line 124 separates each sheet into a first portion 126 and a second portion 128. The first portion 126 is generally elongate in shape relative to the second portion 128 such that, when the sheet is folded along the folding line 124, a pulling edge 130 or tab of the first portion 126 extends over the second portion 128. The pulling edge 130 is gripped mechanically or manually during removal of the sheet from the cassette 100. In some embodiments, the pulling edge 130 includes holes or slots that are mechanically grasped during removal of the sheet from the cassette 100. In some embodiments, the pulling edge 130 extends at least partially outside the cassette 100.

Figure 1B:
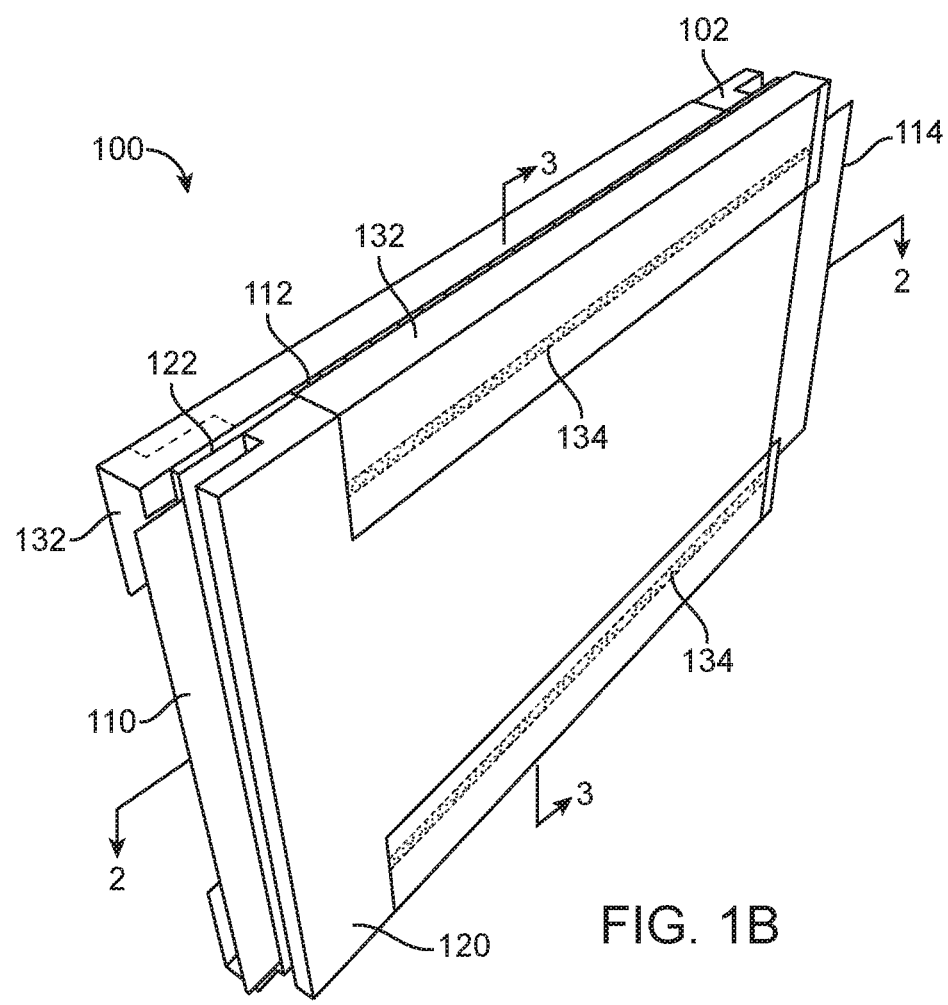

In some embodiments, each sheet further includes one or more wing-shaped sections 132 that are at least partially wrapped around an outer surface of the support. In some embodiments, the wing-shaped section 132 is adhered to an outer surface of the support. In other embodiments, the section 132 is adhered to an edge, a facet or an inner surface of the support. Exemplary techniques that may be used to adhere one or more sections to the support include, but are not limited to, heat sealing, solvent welding, gluing and/or taping. As shown in FIG. 1B, the section 132 may be partially adhered in one or more lines 134 or in spots to the outer surface of the support. In other embodiments, the entire section 132 may be adhered to the outer surface of the support.

In embodiments having sections 132, the sheets 110, 114 include one or more tear lines 136 and optional cutting lines 138 between the sections 132 and the body of the sheet. The tear lines 136 and cutting lines 138 facilitate removal of the sheets from the cassette 100 such that no uneven rips or holes are created in the sheets. Uneven rips or holes in the sheets may cause partial exposure of the gel 112 to the membrane 108 which may result in incomplete transfer of molecules. In an embodiment, the tear line 136 is perforated. In some embodiments, the cutting line 138 separates the first portion 126 from the section 132 and the tear line 136 separates the second portion 128 from the section 132. In some embodiments having no cutting line, the tear line 136 separates both the first and section portions 126,128 from the wing-shaped section 136.

In some embodiments, the sheets are non-conducting and are about 30-50 microns thick. Exemplary materials from which the sheets may be formed include, but are not limited to, acrylic (e.g., acrylate polymer), polyester (e.g., polyethylene terephthalate) or nylon. In some embodiments, a gel-facing surface of each sheet is coated with a barrier coating (e.g., an oxygen impermeable substance) and/or a release agent (e.g., a hydrophilic polymer). In an embodiment, the gel-facing surface of each sheet is treated with a barrier coating that blocks oxygen. Oxygen interferes with polyacrylamide gel polymerization, as described in U.S. patent application Ser. No. 14/085,472, which is incorporated by reference in its entirety herein. In some embodiments, at least one surface of each sheet is treated with polyvinylidene chloride, low-density polyethylene and/or acrylonitrile methyl acetate copolymer. In some embodiments, the barrier coating is polyvinylidene chloride copolymer emulsion (e.g., Serfene™ 411 and/or Serfene™ 2060). In some embodiments, at least one surface of each sheet is coated with a release agent including, but not limited to, polyvinyl acetate, polyethylene glycol and/or starch. Exemplary techniques for applying a barrier coating and/or release agent to one or more surfaces of the sheets include, but are not limited to, spraying, dipping, painting or spin coating.

The membrane 108 provides a surface onto which molecules from the electrophoresis gel are transferred and is located on the side of the cassette 100 having the transfer anode 104. Thus, as shown in FIGS. 1A, 2 and 3, the membrane 108 is sandwiched between the first sheet 110 and the first pad 106. Exemplary materials from which the membrane 108 may be formed include, but are not limited to, nitrocellulose or polyvinylidene fluoride. In some embodiments, the membrane 108 is folded along a folding line located perpendicular to a longitudinal axis of the sheet (not shown). In some embodiments, the membrane 108 includes a gripping edge 140 or tab that extends at least partially outside the cassette 100 to facilitate mechanical or manual extraction of the membrane 108 from the cassette 100 after electrophoretic transfer is complete (see FIG. 2). In certain embodiments, the pulling edge of the membrane 108 includes holes or slots that are mechanically grasped during removal of the membrane 108 from the cassette 100.

Referring again to FIGS. 1A, 2 and 3, the second pad 116 is located between the second sheet 114 and the transfer cathode 118. The first and second pads 106, 116 act as electrode reservoirs for transfer buffer which contains ions that complete the electrical circuit between the transfer anode 104 and transfer cathode 118. In some embodiments, the pads are porous and/or absorbent (e.g., porous plastic, porous polymers or cotton fiber). In an embodiment, the pads are formed from Porex®.

In some embodiments, the pads and transfer membrane are pre-soaked with transfer buffer. In other embodiments, transfer buffer is injected into each pad through a hole in the cassette support.

The transfer electrodes (i.e., the transfer anode 104 and transfer cathode 118) are each sandwiched between a pad and a support. The transfer electrodes 104, 118 are positioned in the cassette 100 such that molecules in the gel migrate toward the transfer anode 104 and onto the membrane 108. The transfer anode 104 is sandwiched between the first pad 106 and the first support 102. In some embodiments, the transfer electrodes 104, 118 are formed from metals including, but not limited to, aluminum, platinum, stainless steel, and/or copper.

As shown in FIG. 1A, the transfer electrodes 104, 118 are planar (e.g. foil or sheets of metal). In other embodiments, each transfer electrode may be a single wire, a plurality of wires or a grid/mesh of wires. In embodiments in which the transfer electrodes are planar, the electrodes may be pitted by the corrosive buffer used for electrophoretic transfer. Corroded electrodes do not contact the pads evenly during blotting, causing uneven transfer and poor results. Electrodes of sufficient thickness will not be pitted through and can be used for multiple transfers. In some embodiments, the thickness of the planar transfer electrodes is between 20 microns and 200 microns.

In some embodiments, the cassette 100 includes a second set of electrodes (e.g., separation electrodes). In certain embodiments, a separation anode and a separation cathode are positioned in the cassette 100 such that molecules in the gel migrate toward the separation anode. As shown FIG. 3, in embodiments in which the gel is oriented vertically, the separation anode 139 is placed in such a way that molecules move in the plane of and down the gel. In a vertically oriented embodiment, the separation anode 139 may be positioned along at least a portion of a lower edge of the gel. In some embodiments, the gel is oriented horizontally and, depending on the placement of the separation anode 139, the molecules can move in multiple directions within the plane of the gel (e.g., left to right, right to left, front to back or back to front). In embodiments, the cassette 100 includes first and second electrode reservoirs configured to hold separation buffer for gel electrophoresis. The first and second electrode reservoirs are located in the plane of and at either end of the separation gel 112 such that the electrical circuit between the separation electrodes can be completed.

In some embodiments, the first and second set of electrodes are controlled by the same circuit, i.e., one circuit is used to apply the same or different voltages across each set of electrodes. In some embodiments, the first set of electrodes is controlled by a different circuit than the second set of electrodes such that the two sets of electrodes can be operated independently.

In some embodiments, the transfer electrodes, pads, membrane and sheets are sized to match the planar dimensions of the gel 112 such that the molecules from the entire gel 112 are transferred. In other embodiments, the planar dimension of the transfer electrodes is larger than that of the pads, membrane and sheets.

The first and second supports 102, 120 form the outermost layer of the cassette 100 and support the stack of components. In an embodiment, each of the supports 102, 120 is molded plastic (e.g., polycarbonate) or polyester (e.g., polyethylene terephthalate). In some embodiments, the supports 102, 120 are formed from glass. In some embodiments, the supports 102, 120 include a recess 142 on an electrode-facing side in which the electrode is disposed. In some embodiments, the supports 102, 120 include one or more longitudinal edges 144 for gripping and to facilitate opening the cassette. In some embodiments, the first support 102 is snap fit to the second support 120. In some embodiments, the first support 102 is hingedly attached to the second support 120.

Methods

Referring to FIGS. 6 and 7A-9B, a method 600 for combined electrophoresis and electroblotting that uses the aforementioned cassette 100 will now be described.

In some embodiments, the method 600 begins by inserting an assembled cassette 100 is into a holder. Samples (i.e., protein or nucleic acid fragment samples) are loaded into wells in the gel 112. A first electric field is applied within the electrophoretic plane of the separation gel 112 to separate proteins or nucleic acid fragments into bands. In some embodiments, at least one lane in the gel 112 is used to monitor the progress of luminescently-labeled molecular weight standard bands as they migrate through the gel 112 and to determine when to stop the electrophoresis. In embodiments in which proteins are being separated, the progress of dye labeled molecular weight standard bands may be monitored visually or colorimetrically. In embodiments in which nucleic acid fragments are being separated, the progress of ethidium bromide labeled molecular weight standard bands may be monitored by ultraviolet light detection.

In an embodiment shown in FIG. 10, the progress of the separation is followed by, for example, a line array detector 146. In some embodiments in which proteins are being separated, a vertically oriented line array detector may be used in real time to monitor the progress of protein separation by colorimetrically detecting protein molecular weight standard bands (e.g., Bio-Rad Precision Plus Protein™ Dual Color Standards) as they migrate through the gel 112. In some embodiments in which proteins are being separated, a horizontally oriented line array detector may be used for detecting a tracking dye (e.g., Bromophenol blue) as the dye reaches an end of the gel 112. In some embodiments in which nucleic acid fragments are being separated, a line array detector that detects ultraviolet light may be used in real time to monitor the progress of nucleic acid fragment separation by detecting nucleic acid molecular weight standard bands as they migrate through the gel 112.

In some embodiments in which two dimensional electrophoresis is used to analyze protein samples, an IPG strip or a single lane polyacrylamide gel having protein bands separated by isoelectric focusing or PAGE, respectively, is applied to the top of gel 112 having no sample wells and an electric field is applied within the electrophoretic plane of the gel 112, resulting in dots or blots instead of bands.

Figure 8A:
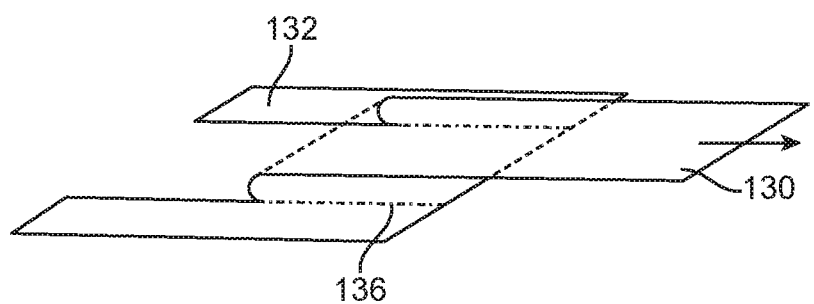
FIGS. 8A and 8B show schematic perspective views of a sheet of FIG. 4B during and after removal from a cassette. For clarity, the sheet is shown without the other cassette components.
Figure 8B:
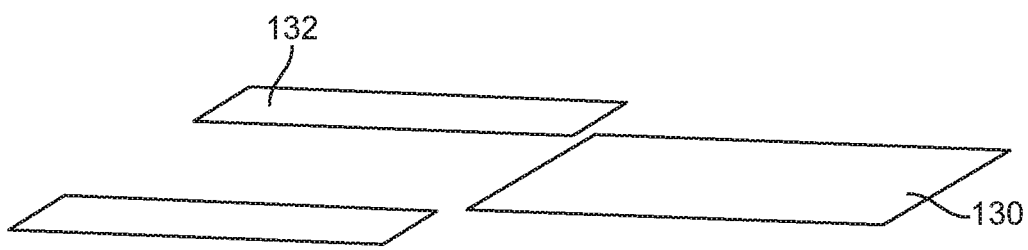
Figure 9A:
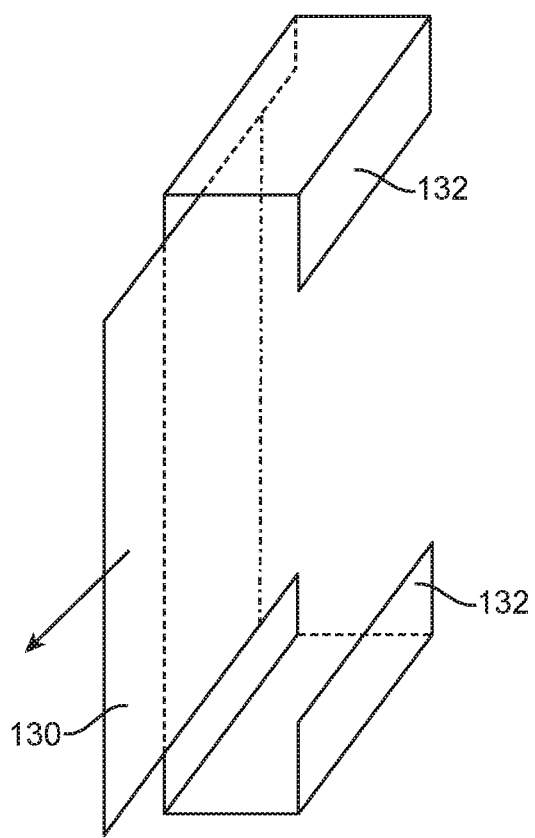
FIGS. 9A and 9B show schematic perspective views of a sheet of FIG. 4B before and after removal from a cassette.
Figure 9B:
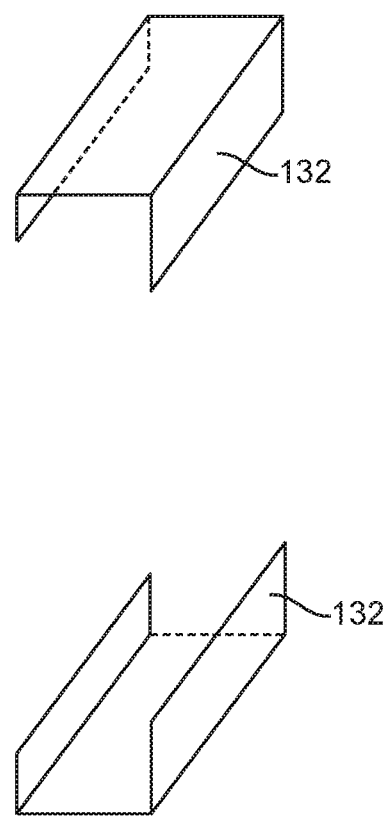

Referring to FIGS. 6, 7A, 8A and 9A, in exemplary step 610, a first and second sheet 110, 114 are removed from an unopened cassette 100 by manually or mechanically pulling on an edge 130 or a tab on each sheet. The force applied to the pulling edge 130 is parallel to the plane of the cassette 100. The pulling edge 130 extends at least partially outside the cassette 100 (see FIG. 7A). The first and second sheets 110, 114 each are folded along a folding line that is perpendicular to the longitudinal axis of the sheet. The fold in each sheet facilitates pealing (rather than pulling) of the sheet from the surface of the gel, which can prevent tears in the gel. As the first sheet 110 is removed from the cassette 100, a membrane 108 is exposed to a first surface 148 of the gel 112 having previously separated molecules. As the second sheet 114 is removed from the cassette 100, a second pad 116 is exposed to a second gel surface 150. The second sheet 114 may be removed concurrent with removal of the first sheet 110 or after the first sheet 110 is removed. Removing the first and second sheets 110, 114 concurrently results in uniform pulling/extraction forces which may avoid uneven tears or holes in the sheets, preventing partial exposure of the gel 112 to the membrane 108 and incomplete transfer of molecules. As shown in FIGS. 7B, 8B and 9B, the edge 130 of each sheet is pulled until the sheet is completely removed from the cassette 100.

In embodiments in which the sheets have a wing-shaped section 132, the sheets are removed by tearing the sheets along perforated tear lines 136.

In some embodiments, a sheet is extracted by first bonding the pulling edge 130 to a cylindrical rod 152 (see FIG. 11). The rod 152 is then pulled in a linear direction that is parallel to the plane of the sheet or is rotated about its longitudinal axis to wind the sheet around the rod 152 in such a way that tears in the sheet are avoided, i.e., by exerting even pulling forces on the sheet.

In exemplary step 620, a second electric field is applied normal to the electrophoretic plane of the separation gel 112 to transfer the molecules to the membrane 108.

In some embodiments, the buffer-soaked membrane 108 is then manually or mechanically extracted from the cassette 100 after the molecules are electrophoretically transferred thereon and prior to further processing (e.g., washing and detection of transferred molecules) of the membrane 108. As shown in FIG. 12, in some embodiments, the buffer-soaked membrane 108 is manually or mechanically extracted by grasping a gripping edge 140 or tab and pulling on the edge 140 until the membrane 108 is removed from the cassette 100.

The molecules transferred to the membrane 108 may then be visualized and/or detected by, for example, secondary labeling detection through the use of detectable moieties and/or labels. In embodiments in which proteins are transferred to a membrane (i.e., Western blotting), primary and/or secondary antibodies are linked to a detection moiety that is detectable by spectrophotometric, photochemical, biochemical, immunochemical, electrical, optical or chemical techniques. In embodiments in which nucleic acid fragments are transferred to the membrane (i.e., Southern or Northern blotting), the nucleic acid probe binding to a target nucleic acid is linked to a detection moiety that is detectable by isotopic, spectrophotometric, photochemical, biochemical, electrical, optical or chemical techniques.

In some embodiments, detection is performed enzymatically using, for example horseradish peroxidase or alkaline phosphatase. In Western blotting embodiments, the detection moiety is a fluorophore including, but not limited to, Alexa dyes (e.g., Alexa 350, Alexa 430, etc.), AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine and/or Texas Red. In some Western blotting embodiments, the detection moiety is an infrared light-absorbing dye including, but not limited to, IRDye 800CW, IRDye 680LT, IRDye, 700DX, and/or IRDye 680. In Southern or Northern blotting embodiments, the detection moiety is a fluorophore including, but not limited to, biotin, fluorescein, DNP, fucose and/or Texas Red.

Systems

Another aspect of the invention is a combined electrophoresis and electroblotting system. The system may be automated or semi-automated. The system as described herein includes the aforementioned cassette 100. In embodiments of the system, one or more voltage sources are operably connected to the first and second set of electrodes and are configured to apply a first electric field within an electrophoretic plane of the separation gel 112 and a second electric field normal to the electrophoretic plane of the separation gel 112. Other components of the system may include, but are not limited to, a power source, computer controlled circuitry that controls the electronic and/or mechanical components, a microprocessor, a memory, and/ or a display.

Referring to FIG. 13, an automated electrophoresis and electroblotting system 1300 that uses the cassette 100 will now be described. The system 1300 includes a container 1350, a first pump 1352, a light source (not shown) and a detector 1354 (e.g., an imager).

The container 1350 is configured to hold the cassette 100, an extractor 1356 for removing the sheets and/or membrane 108 from the cassette 100, and blotting solutions used during processing of the membrane 108. The container 1350 includes a drainage hole 1358 in fluid communication with a waste line 1360. Fluid flow into the waste line 1360 may be controlled by a valve or a second pump 1362.

The container 1350 may be formed of materials that are optically clear such that light may irradiate the membrane 108 from below the container. Exemplary materials from which the container may be formed include, but are not limited to, polystyrene, polycarbonate, allyl diglycol carbonate and/or polymethyl methacrylate.

The first pump is used to pump a plurality of blotting solutions (e.g., buffers, blocking solution, primary/secondary antibody solutions or substrate solution) each from a reservoir 1364 into the container during membrane processing. Each reservoir is in fluid communication with a line. The fluid flow through the lines and to the pump is controlled by at least one valve 1366.

The light source is configured to irradiate the surface of the membrane 108. Depending on the signal to be detected, the light source may provide light ranging from the ultraviolet range to the far infrared range. Exemplary light sources include lasers, light emitting diodes and PL bulbs. In some embodiments, the light source may provide light in multiple wavelength ranges. In some embodiments, the light source is configured to illuminate the membrane 108 by transillumination. In other embodiments, the light source is configured to illuminate the membrane 108 by epi-illumination.

The detector 1354 is configured to detect light emitted from molecules on the surface of the membrane 108 by the molecules having detectable moieties and/or labels. In some embodiments, detection is achieved by colorimetric, fluorescent, phosphorescent, chemiluminescent or isotopic detection. In some embodiments, detection is achieved by imaging such as by photography, by electronic detectors or by isotopic detectors. Exemplary electronic detectors include photodiodes, charge-coupled device (CCD) detectors, or complementary metal-oxide semiconductor (CMOS) detectors.

In operation of the system 1300, the cassette 100 is inserted into the container. Samples (i.e., protein or nucleic acid fragment samples) are loaded into wells 1368 in the separation gel 112 and the molecules are separated by electrophoresis. After electrophoresis is complete, the sheets are removed with the extractor without opening the cassette 100. The transfer membrane 108 on the anode side of the cassette and a pad on the cathode side of the cassette are exposed to the gel 112. The molecules in the gel 112 are next transferred to the membrane 108. Without opening the cassette 100, the membrane 108 is mechanically removed from the cassette 100 with the extractor. After being removed from the cassette 100, the membrane 108 is processed by sequentially pumping various blotting solutions into the container. After the membrane 108 is incubated with each blotting solution, each solution is drained from the container and is sent to waste through the drainage hole 1358. The fluid flow to waste may be controlled by a pump 1362 and/or by a valve.

Target molecules 1370 are then detected by the detector. The analog signal from the detector 1354 is digitized by an analog-to-digital converter 1372. The digitized signal is processed by a microprocessor 1374 to obtain at least one value or intensity of detected light that is store in memory 1376 and/or displayed on an optional display 1378.

By using appropriate electronics and software, the system can be programmed to know the identity and location of target molecules 1370 on the surface of the membrane 108. By using appropriate electronics/components (e.g. a barcode reader) and software, the system may also be programmed to know the identity of the membrane 108 and/or cassette 100 used to analyze the target molecules 1370.

Additional Disclosure and Claimable Subject Matter

Item 1. A cassette comprising:
a separation gel; and
a sheet adjacent to a surface of the separation gel, wherein the sheet is configured to be removed from the cassette without opening the cassette.

Item 2. The cassette of Item 1, wherein the sheet is folded along a folding line.

Item 3. The cassette of Item 2, wherein the sheet further comprises a section.

Item 4. The cassette of Item 3, wherein the section is wing-shaped.

Item 5. The cassette of Item 3 or 4, wherein the section is at least partially wrapped around an outer surface of a support.

Item 6. The cassette of any one of previous Items 3 to 5, wherein the section is adhered to an outer surface of the support.

Item 7. The cassette of any one of previous Items 1 to 6, wherein the sheet comprises a pulling edge.

Item 8. The cassette of any one of previous Items 1 to 6, wherein the sheet comprises a tab.

Item 9. The cassette of any one of previous Items 1 to 8, wherein a gel-facing surface of the sheet is coated with a barrier coating.

Item 10. The cassette of Item 9, wherein the barrier coating is selected from the group consisting of polyvinylidene chloride, low-density polyethylene, and an acrylonitrile methyl acetate copolymer.

Item 11. The cassette of any one of previous Items 10, further comprising a membrane sandwiched between the sheet and a pad.

Item 12. The cassette of Item 11, wherein the membrane is configured to be removed from the cassette without opening the cassette.

Item 13. The cassette of Item 11 or 12, wherein the membrane comprises a pulling edge.

Item 14. The cassette of any one of previous Items 1 to 13, further comprising a set of transfer electrodes.

Item 15. The cassette of any one of previous Items 1 to 13, further comprising a first set of electrodes and a second set of electrodes.

Item 16. The cassette of Item 15, wherein the first set of electrodes are separation electrodes and the second set of electrodes are transfer electrodes.

Item 17. A method comprising:
removing a sheet from a cassette having a separation gel with previously separated molecules, wherein the sheet is configured to be removed from the cassette without opening the cassette; and
responsive to applying an electric field normal to an electrophoretic plane of the separation gel, transferring the molecules to a membrane.

Item 18. The method of Item 17, wherein the sheet is folded along a folding line.

Item 19. The method of Item 17 or 18, wherein the sheet further comprises a section.

Item 20. The method of Item 19, wherein the section is wing-shaped.

Item 21. The method of Item 19 or 20, wherein the section is at least partially wrapped around an outer surface of a support.

Item 22. The method of any one of previous Items 19 to 21, wherein the section is adhered to an outer surface of the support.

Item 23. The method of any of previous Items 17 to 22, wherein the sheet comprises a pulling edge.

Item 24. The method of any of previous Items 17 to 22, wherein the sheet comprises a tab.

Item 25. The method of any of previous Items 17 to 24, wherein a gel-facing surface of the sheet is coated with a barrier coating.

Item 26. The method of Item 25, wherein the barrier coating is selected from the group consisting of polyvinylidene chloride, low-density polyethylene, and an acrylonitrile methyl acetate copolymer.

Item 27. The method of any of previous Items 17 to 26, further comprising a membrane sandwiched between the sheet and a pad.

Item 28. The method of Item 27, wherein the membrane is configured to be removed from the cassette without opening the cassette.

Item 29. The method of Item 27 or 28, wherein the membrane comprises a pulling edge.

Item 30. The method of any of previous Items 17 to 29, further comprising a set of transfer electrodes.

Item 31. The method of any of previous Items 17 to 29, further comprising a first set of electrodes and a second set of electrodes.

Item 32. The method of Item 31, wherein the first set of electrodes are separation electrodes and the second set of electrodes are transfer electrodes.

Item 33. A system comprising:
a cassette comprising:
  a separation gel;
  a sheet adjacent to a surface of the separation gel, wherein the sheet is configured to be removed from the cassette without opening the cassette;
  a membrane sandwiched between the sheet and a pad;
  a first and second set of electrodes; and
circuitry operably connected to the first and second set of electrodes and configured to apply a first electric field within an electrophoretic plane of the separation gel and a second electric field normal to the electrophoretic plane of the separation gel.

Item 34. The system of Item 33, further comprising at least one of a power source, a voltage source, a manual sheet extractor, a motorized sheet extractor, a pump connected to one or more reservoirs, a pump connected to waste, a manual membrane extractor, a motorized membrane extractor, a line array detector and an imager.

Item 35. The system of Items 33 or 34, wherein the sheet is folded along a folding line.

Item 36. The system of any one of previous Items 33 to 35, wherein the sheet further comprises a section.

Item 37. The system of Item 36, wherein the section is wing-shaped.

Item 38. The system of Items 36 or 37, wherein the section is at least partially wrapped around an outer surface of a support.

Item 39. The system of any one of previous Items 36 to 38, wherein the section is adhered to an outer surface of the support.

Item 40. The system of any one of previous Items 33 to 39, wherein the sheet comprises a pulling edge.

Item 41. The system of any one of previous Items 33 to 39, wherein the sheet comprises a tab.

Item 42. The system of any one of previous Items 33 to 41, wherein a gel-facing surface of the sheet is coated with a barrier coating.

Item 43. The system of any one of previous Items 33 to 42, further comprising a membrane sandwiched between the sheet and a pad.

Item 44. The system of any one of previous Items 33 to 43, further comprising a set of transfer electrodes.

Item 45. The system of any one of previous Items 33 to 43, further comprising a first set of electrodes and a second set of electrodes.

Item 46. The system of claim 45, wherein the first set of electrodes are separation electrodes and the second set of electrodes are transfer electrodes.

EXAMPLES

Example 1

Electrophoresis and Electroblotting of Proteins

Materials:
1. Bicor™ 85 AXT (Multi-Plastics Inc.) sheet material having a gel-facing surface coated with Serfene 2060. Sheet material was cut to size to fit a Criterion® cell so that a first portion could be folded over a second portion to create a pulling tab accessible outside the assembled cassette. The folded sheets were also sized to cover the planar surface of a manually cast gel.
2. Supported Nitrocellulose Membrane (0.2 microns, Bio-Rad Cat.#162-0097) sized to cover the planar surface of a manually cast gel. The membrane was also cut so that a pulling tab was accessible outside the assembled cassette.
3. Two Porex® pads (catalog #X-4898; thickness=0.125 inches; average pore size 15-50 microns; polyethylene; hydrophilic) sized to cover the planar surface of a manually cast gel.
4. Bio-Rad 10x separation (running) buffer (Tris/Glycine/SDS) and Bio-Rad Trans-Blot® Turbo™ Transfer Buffer.
5. Two pieces of aluminum foil sized to cover the planar surface of a manually cast gel. The aluminum foil was used for the transfer anode and cathode. Narrow tails of aluminum foil 3 mm wide and 10 cm long were used as electrical terminals. These electrical terminals extended outside the cassette assembly.
6. Two supports from a Bio-Rad Criterion Empty Cassette.
7. Two spacers, a 15 well comb, clips for holding the cassette assembly together, pipette, pipette tips.
8. Ingredients for a 10% polyacrylamide gel and a 4% stacking gel: 30% bis/acrylamide, 1.5 M Tris-HCl pH 8.8, 10% SDS, double distilled water, TEMED, 10% ammonium persulfate (APS)
9. Bio-Rad Precision Plus Protein™ Dual Color Standards
10. Bio-Rad PowerPac™ Basic separation power supply and Horizon Electronics DHR3655D-10 DC power supply Method:
Half of the cassette was a sandwich of one support, aluminum foil (cathode), a Porex® pad and a folded sheet of Bicor™ 85 AXT. The other half of the cassette was a sandwich of one support, aluminum foil (anode), a Porex® pad, a transfer membrane, and a folded sheet of Bicor™ 85 AXT. In preparation for casting the separation gel, the halves of the cassette were clipped together with spacers such that the pulling edges were on opposing sides of the cassette. After clipping the two halves of the cassette together with spacers and placing the cassette in a vertically oriented casting stand, a gel was cast according to Bio-Rad bulletin 6201 "Handcasting Polyacrylamide Gels". A 10% acrylamide separation gel was made of 3.33 ml of 30% bis/acrylamide, 2.5 ml of 1.5M Tris-HC1 pH 8.8, 100 uL of 10% SDS, 4.02 ml of double distilled water, 5 uL of Temed and 50 uL of 10% APS. A 4% stacking gel was made of 0.66 ml of 30% bis/acrylamide, 1.26 ml of 1.5M Tris-HC1 pH 6.8, 50 uL of 10% SDS, 3 mL of double distilled water, 5 uL of Temed and 25 uL of 10% APS. The 15 well comb was used to make sample wells in the stacking gel.

The assembled cassette was placed into a Bio-Rad Criterion® cell. Bio-Rad separation buffer (Tris/Glycine/SDS Buffer) prepared according to the kit instructions was placed in the upper and lower reservoirs of the Criterion® cell. Ten microliters of Bio-Rad Precision Plus Protein™ Dual Color Standards was loaded into each of the 15 sample wells. SDS PAGE was carried out by applying 250 Volts across the separation electrodes for about 17 minutes with a Bio-Rad PowerPac™ Basic separation power supply set at constant voltage mode. Current was about 60 mAmp.

When SDS PAGE was complete, the cassette was removed from the Criterion cell. The two folded sheets were removed one at a time from the cassette by manually grasping the edge of each sheet and then pulling on the edge until each sheet was removed.

To transfer the color protein bands to the membrane, transfer buffer was injected into each side of the cassette through a small hole in each support. The cassette was then placed in a horizontal orientation and the electrical terminals of the transfer electrodes were attached to a Horizon Electronics DHR3655D-10 DC power supply. The separated proteins were transferred to the membrane by applying 25 volts across the transfer electrodes for about 4 minutes at constant voltage mode (current was about 0.35 Amps).

The colored bands of transferred protein from the Dual Color standards were visualized without further processing of the membrane.

Example 2

Electrophoresis and Electroblotting of RNA Fragments

Materials
1. Bicor™ 85 AXT (Multi-Plastics Inc.) sheet material having a gel-facing surface coated with Serfene 2060. Sheet material was cut to size to fit a Bio-Rad Criterion® cell so that a first portion could be folded over a second portion to create a pulling tab accessible outside the assembled cassette. The folded sheets were also sized to cover the planar surface of a manually cast gel.
2. Nylon Membrane (Bio-Rad Zeta-Probe GT Membranes) sized to cover the planar surface of a manually cast gel. The membrane was also cut so that a pulling tab was accessible outside the assembled cassette.
3. Whatman 3MM Chr paper sized to cover the planar surface of a manually cast gel.
4. Bio-Rad 10× TBE (for both separation and Northern transfer buffer), TBE-urea (denaturing) sample buffer (includes Bromophenyl Blue and Xylene Cyanol FF tracking dyes).
5. Two pieces of aluminum foil sized to cover the planar surface of a manually cast gel. The aluminum foil was used for the transfer anode and cathode. Narrow tails of aluminum foil 3 mm wide and 10 cm long were used as electrical terminals. These electrical terminals extended outside the cassette assembly.
6. Two supports from a Bio-Rad Criterion Empty Cassette.
7. Two spacers, a 15 well comb, clips for holding the cassette assembly together, pipette, pipette tips.
8. Ingredients for a 12.5% polyacrylamide gel: 40% bis/acrylamide, 10x TBE, double distilled water, TEMED, 30% ammonium persulfate (APS).
9. New England BioLabs Low Range ssRNA Ladder (sizes range from 1000 to 50 bases).
10. Bio-Rad PowerPac™ Basic separation power supply and Horizon Electronics DHR3655D-10 DC power supply.
11. Life Technologies SYBR Green II RNA stain.
12. Bio-Rad ChemiDoc MP.

Half of the cassette is a sandwich of one support, aluminum foil (cathode), a piece of Whatman 3 MM Chr paper and a folded sheet of Bicor™ 85 AXT. The other half of the cassette is a sandwich of one support, aluminum foil (anode), a piece of Whatman 3 MM Chr paper, the nylon transfer membrane, and a folded sheet of Bicor™ 85 AXT. In preparation for casting the separation gel, the halves of the cassette are clipped together with spacers such that the pulling edges are on opposing sides of the cassette. After clipping the two halves of the cassette together with spacers and placing the cassette in a vertically oriented casting stand, a denaturing polyacrylamide gel is cast. A Ten milliliters of the following are mixed together to make a denaturing 12.5% acrylamide separation gel: 4.8 grams urea, 3.125 ml of 40% bis/acrylamide, 4 uL of TEMED, 30 uL of 10% APS, 1 ml 10x TBE, fill to volume with double distilled water. The 15 well comb is used to make sample wells in the gel.

The assembled cassette was placed into a Bio-Rad Criterion® cell. Bio-Rad TBE separation buffer prepared according to the kit instructions is placed in the upper and lower reservoirs of the Criterion® cell. 10 microliters of the Low Range ssRNA Ladder is mixed with 10 microliters of TBE-urea sample loading buffer. This diluted ladder solution is heat denatured by heating the solution between 70-90° C. for a few minutes. Before loading the diluted ladder, the gel is pre-run at 15-25 W (constant watt mode) for 30 minutes to heat the gel up 1.0 microliters of the denatured ssRNA ladder is then loaded into each of the 15 sample wells. PAGE is carried out at 40 mAmp for about 60 minutes with a Bio-Rad PowerPac™ Basic separation power supply set at constant current mode.

When PAGE is complete (i.e., the tracking dye is at the bottom of the gel), the cassette is removed from the Criterion® cell. The two folded sheets are removed one at a time from the cassette by manually grasping the edge of each sheet and then pulling on the edge until each sheet is removed.

The cassette is then placed in a horizontal orientation and the electrical terminals of the transfer electrodes are attached to a Horizon Electronics DHR3655D-10 DC power supply. The RNA bands are transferred to the membrane at 250 mAmps for about 2 hours (constant current mode).

The bands of the transferred ladder are visualized by SYBR Green II RNA stain with 254 nm transillumination using the Bio-Rad ChemiDoc MP.

The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A cassette comprising:
   a separation gel; and
   a sheet adjacent to a surface of the separation gel, wherein the sheet is configured to be removed from the cassette without opening the cassette, wherein the sheet is folded along a folding line and wherein portions of the sheet on either side of the folding line are in contact with each other and between the gel and a cassette wall.

2. The cassette of claim 1, wherein the sheet further comprises a section that is at least partially wrapped around an outer surface of a support.

3. The cassette of claim 2, wherein the section is wing-shaped.

4. The cassette of claim 3, wherein the section is adhered to an outer surface of the support.

5. The cassette of claim 1, wherein the sheet comprises a pulling edge.

6. The cassette of claim 1, wherein the sheet comprises a tab.

7. The cassette of claim 1, wherein a gel-facing surface of the sheet is coated with a barrier coating.

8. The cassette of claim 7, wherein the barrier coating is selected from the group consisting of polyvinylidene chloride, low-density polyethylene, and an acrylonitrile methyl acetate copolymer.

9. The cassette of claim 1, further comprising a membrane sandwiched between the sheet and a pad.

10. The cassette of claim 9, wherein the membrane is configured to be removed from the cassette without opening the cassette.

11. The cassette of claim 10, wherein the membrane comprises a pulling edge.

12. The cassette of claim 1, further comprising a set of transfer electrodes.

13. The cassette of claim 1, further comprising a first set of electrodes and a second set of electrodes.

14. The cassette of claim 13, wherein the first set of electrodes are separation electrodes and the second set of electrodes are transfer electrodes.

15. A method comprising:
    removing a sheet from a cassette having a separation gel with previously separated molecules, wherein the sheet is configured to be removed from the cassette without opening the cassette; and
    responsive to applying an electric field normal to an electrophoretic plane of the separation gel, transferring the molecules to a membrane.

16. A system comprising:
    a cassette comprising:
    a separation gel;
    a sheet adjacent to a surface of the separation gel, wherein the sheet is configured to be removed from the cassette without opening the cassette;
    a membrane sandwiched between the sheet and a pad;
    a first and second set of electrodes; and
    circuitry operably connected to the first and second set of electrodes and configured to apply a first electric field within an electrophoretic plane of the separation gel and a second electric field normal to the electrophoretic plane of the separation gel.

17. A cassette comprising:
    a separation gel;
    a sheet adjacent to a surface of the separation gel, wherein the sheet is configured to be removed from the cassette without opening the cassette, and
    a membrane sandwiched between the sheet and a pad.

18. The cassette of claim 17, wherein the membrane is configured to be removed from the cassette without opening the cassette.

19. The cassette of claim 18, wherein the membrane comprises a pulling edge.

* * * * *